(12) United States Patent
Duan et al.

(10) Patent No.: US 8,946,457 B2
(45) Date of Patent: Feb. 3, 2015

(54) FLAVONE DERIVATIVES AND THEIR PREPARATIVE METHOD AND MEDICAL USE

(75) Inventors: Hongquan Duan, Tianjin (CN); Nan Qin, Tianjin (CN); Wenyan Niu, Tianjin (CN); Meina Jin, Tianjin (CN); Lihuan Shi, Tianjin (CN); Ying Chen, Tianjin (CN)

(73) Assignee: Tianjin Medical University, Tianjin (CN)

( * ) Notice: Subject to any disclaimer, the term of this patent is extended or adjusted under 35 U.S.C. 154(b) by 3 days.

(21) Appl. No.: 13/885,063

(22) PCT Filed: Nov. 12, 2010

(86) PCT No.: PCT/CN2010/001818
§ 371 (c)(1),
(2), (4) Date: May 13, 2013

(87) PCT Pub. No.: WO2012/061958
PCT Pub. Date: May 18, 2012

(65) Prior Publication Data
US 2013/0231492 A1    Sep. 5, 2013

(51) Int. Cl.
*C07D 311/00* (2006.01)
*C07D 311/30* (2006.01)
*A61K 31/35* (2006.01)

(52) U.S. Cl.
CPC .............. *C07D 311/30* (2013.01); *A61K 31/35* (2013.01)
USPC .......................................... 549/403; 514/460

(58) Field of Classification Search
CPC ............................. C07D 311/30; A61K 31/35
USPC .......................................... 549/403; 514/460
See application file for complete search history.

(56) References Cited

FOREIGN PATENT DOCUMENTS

CN        1916012 A      2/2007
JP        2004-217545 A  8/2004

OTHER PUBLICATIONS

Shi et al Diabete. Res. & Clinc. Prac. (2011) p. 41-46.*
Qin et al, Euro. Jol. Med. Chem. vol. 46 (2011) pp. 5189-5195.*
Shi et al, Diabetes Research and Clinical Practice vol. 92 pp. e42-e46 (2011).*
Jung et al., "Effect of Citrus Flavonoids on Lipid Metabolism and Glucose-Regulating Enzyme mRNA Levels in Type-2 Diabetic Mice," Int'l J. of Biochem. & Cell Biol., vol. 38, pp. 1134-1145 (2006).
Ong et al., "Insulinometic Effects of Myricetin on Lipogenesis and Glucose Transport in Rat Adipocytes but not Glucose Transporter Translocation," Biochem. Pharmacol., vol. 51, pp. 423-429 (1996).
Vessal et al., "Antidiabetic Effects of Quercetin in Streptozocin-Induced Diabetic Rats,"Comp. Biochem. & Phys. Part C, vol. 135, pp. 357-364 (2003).
de Sousa et al., "Hypoglycemic Effect and Antioxidant Potential of Kaempferol-3,7-O-(α)-dirhamnoside from *Bauhinia forficata* Leaves," J. Nat. Prod., vol. 67, pp. 829-832 (2004).
Yoshikawa et al., "Antidiabetic Principles of Natural Medicines II. Aldose Reductase and α-Glocusidase Inhibitors from Brazilian Natural Medicine, the Leaves of *Myrcia multiflora* DC. (Myrtaceae): Structures of Myrciacitrins I and II and Myrciaphenones A and B," Chem. Pharm. Bull., vol. 46, No. 1, pp. 113-119 (1998).
Li et al., "Effect of Puerarin on Insulin Resistance in Diabetic Mice," Chinese Trad. Herbs & Drugs, vol. 37, No. 6, pp. 901-904 (2006).

* cited by examiner

*Primary Examiner* — Noble Jarrell
*Assistant Examiner* — Raymond Covington
(74) *Attorney, Agent, or Firm* — Muncy, Geissler, Olds & Lowe, P.C.

(57) ABSTRACT

Flavone derivatives, preparative method of the derivatives and use thereof as medicaments for treating diabetes. The structure of the derivatives is presented by formula 1: In the structure, $R_1$ and $R_2$, which are identical or not, represent hydrogen atom, halogen, cyano, hydroxyl, trifluoromethyl, thio-methyl, benzyloxy. C1-C8 linear chain or branch chain alkyl, C1-C8 linear chain or branch chain alkoxy. The pharmacological test indicates that the flavone derivatives can significantly increase the glucose consumption of Hep-G2 cell with insulin resistance activity, promote translocation of glucose transporter 4 of skeletal muscle cells (L6GLUT4myc) at different level, and significantly increase glucose intake and utilization by cells. The test proves the fact for the first time that the flavone derivatives can significantly promote translocation of glucose transporter 4 of skeletal muscle cells, and one of the mechanisms for treating diabetes is activating the cell AMPK phosphorylation and phosphorylating the downstream ACC.

17 Claims, 4 Drawing Sheets

FLAVONE DERIVATIVES AND THEIR PREPARATIVE METHOD AND MEDICAL USE

This application is a national stage of International Application No.: PCT/CN2010/001818, which was filed on Nov. 12, 2010, and which is herein incorporated by reference.

TECHNICAL FIELD

The present invention relates to a class of new flavonoid derivative compounds, preparation method and its application as anti-diabetic drug. It belongs to the field of medicinal chemistry.

BACKGROUND OF THE INVENTION

Diabetes mellitus is a group of endocrine and metabolic common disease with coexistence of hyperglycemia and complications which are caused by absolute or relative lack of insulin. It can be divided into type 1 and type2 diabetes, which is a serious harm to human health chronic lifelong disease. Diabetes is not an incurable disease, but so far, there is no radical cure for diabetes up to now. Since the beginning of the 1990s in 2.0 century, with the development of society and population aging, diabetes has been the second position only to cancer, cardiovascular and cerebrovascular diseases in industrialized countries and become a worldwide disease which concerned about major public health problem. In China, the incidence rate rose to 3.21% from 0.67% in 15 years ago, the prevalence of major cities has reached 5 to 6%, and diabetes patients have more than 40 million. Current clinical drugs that commonly used are biguanides, sulfonylureas, α-glucosidase inhibitors, thiazolidinediones, and GLP-1R agonist peptide drugs. Due to the stable and sustained hypoglycemic effects, the metformin becomes one of the essential drugs for the treatment of diabetes. Although the synthetic drugs that are available in the market have significant hypoglycemic effect, they also have some side effects and cannot be effective in preventing the occurrence of complications with long-term use. Therefore, searching for the candidate drug with multi-target effects and preventing complications from natural source have the very important practical significance and high applicable value.

The inventors have found that some flavonoids have anti-diabetes effects. Such as Jung etc. (Effect of citrus flavonoids on lipid metabolism and glucose-regulating enzyme mRNA levels in type-2 diabetic mice, IJBCB, 2006, 38, 1134-1145.), Ong etc. (Insulinomimetic effects of myricetin on lipogenesis and glucose transport in rat adipocytes but not glucose transport translocation. Biochem Pharmacol. 1996, 51(4):423-429.), Mahmood etc. (Antidiabetic effects of quercetin in streptozocin-induced diabetic rats, Comparative Biochemistry and Physiology Part C 135 (2003) 357-'364.) and Eliandra de Sousa etc. (Hypoglycemic Effect and Antioxidant Potential of Kaempferol-3,7-O-(r)-dirhamnoside from Bauhinia forficata Leaves, J. Nat. Prod. 2004, 67, 829-832.) have reported that several flavonoids, hesperidin, myricetin, etc, have the effects improving the lipid metabolism and insulin-like effects. Yoshikawa etc. have reported that myricetin and quercetin has the inhibition effects on α-glucosidase [Antidiabetic principles of natural medicines. II. Aldose reductase and alpha-glucosidase inhibitors from Brazilian natural medicine, the leaves of Myrciamultiflora DC. (Myrtaceae): structures of myrciacitrins I and II and myrciaphenones A and B. Chem Pharm Bull (Tokyo), 1998, 46(1):113-119]. Cao Li et at also have reported that the puerarin has anti-diabetic effect. [Effect of puerarin on insulin resistance in diabetic mice, Chinese Traditional and Herbal Drugs, 2006, 37 (6): 901-904]. However, the above compounds have poor clinical significance due to their weak effects and large doses. In addition, some of them are the lack of a comparison of the positive control drug. A patent (ZL200610015591.5, CN) published by our group reported an anti-diabetic constituent-tiliroside which isolated from *Potentillachinensis*, its structure is shown in Formula (1). The research on tiliroside through pharmacokinetics reveals that the part of glucose in the structure are the pharmacokinetics (prolong the metabolism), yet the kaempferol and cinnamoyl fragments are the pharmacophores. Therefore, on the basis of above consideration, the present invention discloses the synthesis of ether derivatives between cinnamoyl and kaempferol fragments. It is gratifying that the flavonoid derivatives have been found to exhibit comparable or stronger activity with that of metformin, and one of the molecular mechanism on anti-diabetic effect has been clarified. The flavonoid derivatives have the important application in the development of new anti-diabetic drug.

Formula 1

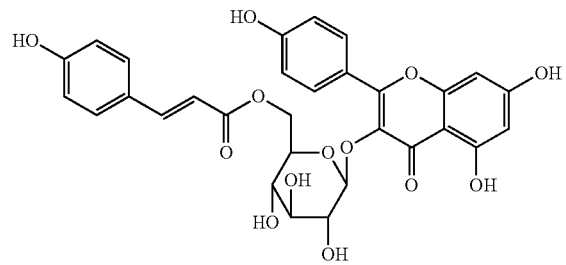

SUMMARY OF THE INVENTION

The present invention provides an anti-diabetic flavonoid compounds, as well as their application in anti-diabetic drug.

The present invention is achieved by the follow technical plan:

In the first aspect, the present invention provides a type of flavonoid derivatives in formula (2), or a pharmaceutically acceptable salt thereof, wherein:

Formula 2

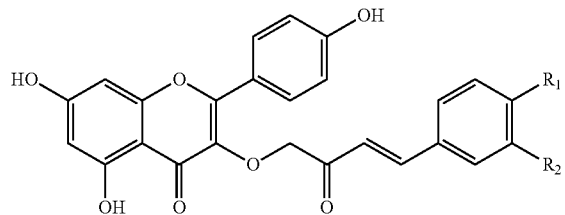

$R_1$ and $R_2$ are the same or different, each independently represents hydrogen, halogen, cyano, hydroxy, benzyloxy, linear or branched chain alkyl of $C_1$-$C_8$, linear branched chain alkyl with halogen substituted of $C_1$-$C_8$ or linear or branched chain alkoxy of $C_1$-$C_8$.

As used herein, for example, $C_1$-$C_8$ alkyl is used to mean an alkyl having 1-8 carbons—that is, 1, 2, 3, 4, 5, 6, 7 or 8 carbons in a linear or branched chain. $C_{1-8}$ alkyl with halogen substituted is used to mean an alkyl with halogen substituted having 1-8 carbons—that is, 1, 2, 3, 4, 5, 6, 7 or 8 carbons in a straight or branched chain. $C_{1-8}$alkoxy is used to mean an alkoxy having 1-8 carbons—that is, 1, 2, 3, 4, 5, 6, 7 or 8 carbons in a linear or branched chain.

Preferably R2 is hydrogen, hydroxyl, $C_{1-8}$alkoxy in a linear or branched chain, more preferably R2 is hydrogen.

The halogen is directed to fluorine, chlorine, bromine or iodine, more preferably the halogen is fluorine or chlorine, The $C_{1-8}$alkyl, $C_{1-8}$alkyl with halogen substituted or $C_{1-8}$alkoxy is preferably having 1, 2, 3 or 4 carbons, more preferably it is having 1 or 2 carbons.

The $C_{1-8}$alkyl with halogen substituted is preferably trifluoromethyl.

In the second aspect, the structure of flavonoid is preferably directed to the following formula:

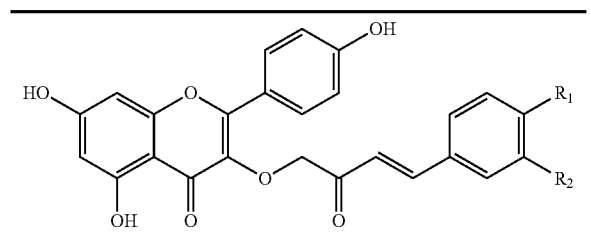

| | R₁ | R₂ |
|---|---|---|
| I-1 | OH | H |
| I-2 | OBn | H |
| I-3 | OMe | H |
| I-4 | OCH₂CH₃ | H |
| I-5 | H | H |
| I-6 | CH₃ | H |
| I-7 | OMe | OH |
| I-8 | OH | OMe |
| I-9 | t-Bu | H |
| I-10 | i-Pr | H |
| I-11 | OH | Cl |
| I-12 | CN | H |
| I-13 | Br | H |
| I-14 | F | H |
| I-15 | Cl | H |
| I-16 | Cl | Cl |

The preferably flavonoid compounds are I-1, I-2, I-3, I-4, I-5, I-6, I-9, I-10, I-12, I-13, and I-14, more preferably compounds are I-3, I-4, I-6, I-9, I-10 and I-12, the most preferably compound is I-12.

In another embodiment, the present invention also provides the preparative method of the flavonoid compounds or a pharmaceutically acceptable salt thereof. The compounds of Formula (2) are synthesized as shown in FIG. 4.

Preferably, flavonoid compounds of Formula (2) or a pharmaceutically acceptable salt thereof can be prepared by the following steps:

(1) To a solution of substituted benzaldehydes in acetone at room temperature was slowly added a solution of the 4N NaOH aqueous solution. The mixture was stirred at 25-40° C. in 15 min-12 h. After completion of the reaction, excess acetone was removed under reduced pressure. Adjusting the pH value is neutral, the reaction mixture was extracted with ethyl acetate, and then the solution was dried over anhydrous MgSO₄. After filtration, the solvent of filtrate was removed, and the crude product was purified by the recrystallization or the column chromatography to give compound series II.

(2) To a solution of compound II in THF at room temperature was slowly added a solution of the pyrrolidonehydrotribromide in THF. The mixture was stirred at room temperature. After completion of the reaction, removal of the solvent afforded crude product, which was chromatographed on silica gel to give the compound series III.

(3) To a mixture of kaempferol and K₂CO₃ in 1,4-dioxane, which was stirred for 1 h while maintaining gentle reflux, was added a solution of the compounds III in 1,4-dioxane for 1.5 h-12 h. The reaction mixture was refluxed until the starting material disappeared. The solvent was removed from the reaction mixture under reduced pressure. Water was added, the aqueous phase was acidification, and then extracted with ethyl acetate. The organic phase was dried, filtered and concentrated. The crude product was purified using a gel-permeation to chromatograph and preparation-TLC to give compound series I.

In the third aspect, the present invention also provides the application of the flavonoid compounds or a pharmaceutically acceptable salt thereof in the pharmaceutical industry, especially in the application for preparing anti-diabetic drug.

In the fourth aspect, the present invention also provides the application of the fiavonoid compounds or a pharmaceutically acceptable salt thereof in the preparing anti-diabetic drug associated with the insulin resistant.

In another embodiment, the present invention also provides the application of the flavonoid compounds or a pharmaceutically acceptable salt thereof in the preparing anti-diabetic drug associated with the glucose transport 4 in the skeletal muscle cells.

In addition, the present invention also provides the application of the flavonoid compounds or a pharmaceutically acceptable salt thereof in the preparing anti-diabetic drug associated AMP-activated protein kinase.

DESCRIPTION OF EMBODIMENTS

Figure 1:
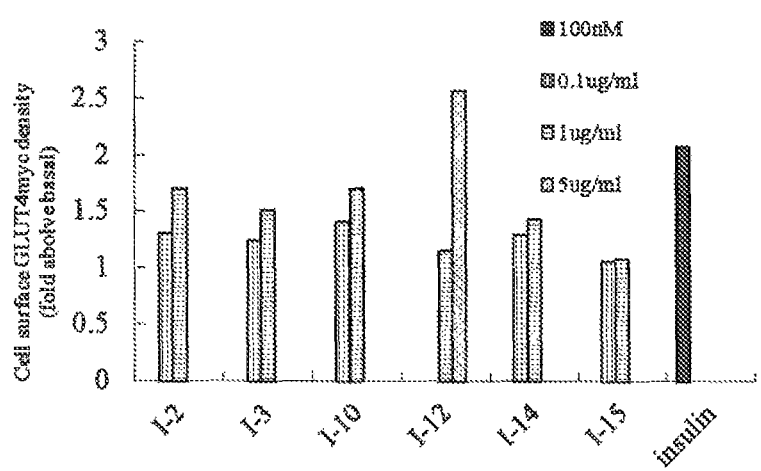
FIG. 1. Promoting effects of flavonoid derivatives on GLUT4myc translocation in the skeletal muscle cells.

The contents of the present invention are specifically described by the following Examples. In the present invention, examples are described in the following in order to illustrate the present invention better, and are not intended to limit the scope of the present invention.

Example 1

General Procedure for the Synthesis of Compounds II

To a solution of substituted benzaldehydes in acetone at room temperature was slowly added a solution of the 4N NaOH aqueous solution. The mixture was stirred at 40° C. After completion of the reaction, excess acetone was removed under reduced pressure. Upon acidification with 1 N HCl, the reaction mixture was extracted with CH₂Cl₂, and then the solution was dried over anhydrous MgSO₄. Solvent was removed, and the crude product was chromatographed on silica gel to give the compound series II shown in Formula (4).

Formula 4

II

| | $R_1$ | $R_2$ |
|---|---|---|
| II-1 | OH | H |
| II-2 | OBn | H |
| II-3 | OMe | H |
| II-4 | OCH$_2$CH$_3$ | H |
| II-5 | H | H |
| II-6 | CH$_3$ | H |
| II-7 | OMe | OH |
| II-8 | OH | OMe |
| II-9 | t-Bu | H |
| II-10 | i-Pr | H |
| II-11 | OH | Cl |
| II-12 | CN | H |
| II-13 | Br | H |
| II-14 | F | H |
| II-15 | Cl | H |
| II-16 | Cl | Cl |

Example 2

General Procedure for the Synthesis of Compounds III

To a solution of compound II in THF at room temperature was slowly added a solution of the pyrrolidonehydrotribromide in THF. The mixture was stirred at room temperature for 24 h. After completion of the reaction, removal of the solvent afforded crude product, which was chromatographed on silica gel to give compound series III shown in Formula (5).

Formula 5

III

| | $R_1$ | $R_2$ |
|---|---|---|
| III-1 | OH | H |
| III-2 | OBn | H |
| III-3 | OMe | H |
| III-4 | OCH$_2$CH$_3$ | H |
| III-5 | H | H |
| III-6 | CH$_3$ | H |
| III-7 | OMe | OH |
| III-8 | OH | OMe |
| III-9 | t-Bu | H |
| III-10 | i-Pr | H |
| III-11 | OH | Cl |
| III-12 | CN | H |
| III-13 | Br | H |
| III-14 | F | H |
| III-15 | Cl | H |
| III-16 | Cl | Cl |

Example 3

General Procedure for the Synthesis of Compounds I

To a mixture of kaempferol (1.2 eq) and K$_2$CO$_3$ (1.2 eq) in 1,4-dioxane (10 ml), which was stirred for 90 minutes while maintaining gentle reflux, was added a solution of the compound III (1 eq) in 1,4-dioxane (2 ml) for 30 minutes. The reaction mixture was refluxed until the starting material disappeared, as indicated by TLC. The solvent was removed from the reaction mixture under reduced pressure. Water was added, the aqueous phase was neutralized (to pH 7) with 1 M HCl, and then extracted with ethyl acetate. The organic phase was dried over anhydrous magnesium sulfate, filtered and concentrated. The crude product was purified using a gel-permeation chromatograph (HW-40; CH$_2$Cl$_2$-MeOH, 1:1) and preparation-TLC to give compound series I as shown in Formula (6).

3.1 The synthesis of 3-O-[(E)-4-(4-Hydroxyphenyl)-2-oxobut-3-en-1-yl] kaempferol (I-1)

After the above mentioned procedure (Example 3), the yellow solid was afforded from compound III-1 as starting material. Yield: 18.5%. $^1$H-NMR (400 MHz, DMSO-d$_6$): δ 12.56 (1H, s, OH), 10.27 (1H, hr s, OH), 10.12 (1H, br s, OH), 8.05 (2H, d, J=8.9 Hz), 7.59 (1H, d, =16.1 Hz), 7.52 (2H, d, J=8.6 Hz), 6.92 (2H, d, T=8.9 Hz), 6.84 (1H, d, J=16.1 Hz), 6.81 (2H, d, J=8.6 Hz), 6.47 (1H, d, J=2.1 Hz), 6.22 (1H, d, J=2.0 Hz), 5.02 (2H, s). $^{13}$C-NMR (100 MHz, DMSO-d$_6$): δ 194.6, 178.0, 164.7, 161.6, 160.7, 156.8, 155.7, 143.6, 136.8, 131.2, 131.0, 125.6, 121.0, 119.3, 116.4, 116.0, 104.5, 99.1, 94.2, 75.6, 60.2. ESI-MS m/z: 445.3 [M-H]$^-$.

3.2 The synthesis of 3-O-[(E)-4-(4-(Benzyloxyphenyl))-2-oxobut-3-en-1-yl] kaempferol (I-2)

After the above mentioned procedure (Example 3), the yellow solid was afforded from compound III-2 as starting material. Yield: 21.3%. $^1$H-NMR (400 MHz, DMSO-d$_6$): δ 12.57 (1H, s, OH), 10.90 (1H, hr s, OH), 10.28 (1H, hr s, OH), 8.05 (2H, d, J=8.9 Hz), 7.65-7.61 (3H, m), 7.47-7.45 (2H, m), 7.42-7.38 (2H, m), 7.36-7.32 (1H, m), 7.07 (2H, d, J=8.8 Hz), 6.94-6.90 (3H, in), 6.47 (1H, d, J=2.0 Hz), 6.22 (1H, d, J=2.0 Hz), 5.16 (2H, s), 5.04 (2H, s). $^{13}$C-NMR (100 MHz, DMSO-d$_6$): δ 194.7, 178.0, 164.7, 161.6, 161.0, 160.7, 156.8, 155.7, 143.0, 137.1, 136.8, 131.0, 130.9, 128.9, 128.4, 128.3, 127.4, 121.0, 120.5, 116.0, 115.8, 104.5, 99.1, 94.2, 75.6, 69.9. ESI-MS m/z: 535.5 [M-H]$^-$.

3.3 The synthesis of 3-O-[(E)-4-(4-Methoxyphenyl)-2-oxobut-3-en-1-yl] kaempferol (I-3)

A After the above mentioned procedure (Example 3), the yellow solid was afforded from compound III-3 as starting material. Yield: 19.2%. $^1$H-NMR (400 MHz, DMSO-d$_6$): δ 12.57 (1H, s, OH), 10.89 (1H, hr s, OH), 10.29 (1H, br s, OH), 8.05 (2H, d, =8.9 Hz), 7.63 (1H, d, J=16.1 Hz), 7.63 (2H, d, J=8.8 Hz), 6.98 (2H, d, J=8.8 Hz), 6.92 (2H, d, J=8.9 Hz), 6.91 (1H, d, J=16.4 Hz), 6.46 (1H, d, J=2.0 Hz), 6.22 (1H, d, J=2.0 Hz), 5.04 (2H, s), 3.80 (3H, s). $^{13}$C-NMR (100 MHz, DMSO-d$_6$): δ 194.7, 178.0, 164.7, 161.9, 161.6, 160.7, 156.8, 155.7, 143.1, 136.7, 131.0, 127.2, 121.0, 120.3, 116.0, 114.9, 104.5, 99.1, 94.2, 75.6, 55.8. ESI-MS m/z: 459.3 [M-H]$^-$.

3.4 The synthesis of 3-O-[(E)-4-(4-Ethoxyphenyl)-2-oxobut-3-en-1-yl] kaempferol (I-4)

After the above mentioned procedure (Example 3), the yellow solid was afforded from compound III-4 as starting material. Yield: 17.3%. $^1$H-NMR (400 MHz, DMSO-d$_6$): δ 12.57 (1H, s, OH), 10.90 (1H, s, OH), 10.28 (1H, s, OH), 8.05 (2H, d, J=8.7 Hz), 7.63 (1H, d, J=16.5 Hz), 7.61 (2H, d, J=8.5 Hz), 7.29 (2H, d, J=8.0 Hz), 6.97 (2H, d, J=8.6 Hz), 6.93 (2H, d, J=8.5 Hz), 6.90 (1H, d, J=14.6 Hz), 6.47 (1H, d, J=1.5 Hz), 6.22 (1H, d, J=1.5 Hz), 5.04 (2H, s), 4.07 (2H, q), 1.34 (3H, t). $^{13}$C-NMR (100 MHz, DMSO-d$_6$): δ 194.2, 177.5, 164.2, 161.1, 160.7, 160.2, 156.3, 155.2, 142.6, 136.3, 130.5, 130.4, 126.5, 121.1, 120.5, 119.7, 115.5, 114.8, 104.0, 98.6, 93.7, 75.2, 63.3, 14.5. ESI-MS m/z: 473.4 [M-H]$^-$.

3.5 The synthesis of 3-O-[(E)-(2-Oxo-4-phenylbut-3-en-1-yl)] kaempferol (I-5)

After the above mentioned procedure (Example 3), the yellow solid was afforded from compound III-5 as starting material. Yield: 17.6%. $^1$H-NMR (400 MHz, DMSO-d$_6$): δ 12.56 (1H, s, OH), 10.89 (1H, s, OH), 10.27 (1H, s, OH), 8.05 (2H, d, J=8.8 Hz), 7.67 (1H, d, J=16.0 Hz), 7.69-7.67 (2H, m), 7.45-7.43 (3H, m), 7.05 (1H, d, J=16.4 Hz), 6.93 (2H, d, J=8.8 Hz), 6.47 (1H, d, J=1.9 Hz), 6.22 (1H, d, J=1.9 Hz), 5.08 (2H, s). $^{13}$C-NMR (100 MHz, DMSO-d$_6$): δ 194.9, 178.0, 164.7, 161.6, 160.7, 156.8, 155.7, 143.1, 136.8, 134.7, 131.2, 131.0, 129.4, 129.0, 122.8, 121.0, 116.0, 104.5, 99.1, 94.2, 75.7. ESI-MS m/z: 429.4 [M-H]$^-$.

3.6 The synthesis of 3-O-[(E)-(2-Oxo-4-(p-tolyl)but-3-en-1-yl)] kaempferol (I-6)

After the above mentioned procedure (Example 3), the yellow solid was afforded from compound III-6 as starting material. Yield: 13.4%. $^1$H-NMR (400 MHz, DMSO-d$_6$): δ 12.56 (1H, s, OH), 10.88 (1H, br s, OH), 10.27 (1H, br s, OH), 8.05 (2H, d, J=8.9 Hz), 7.63 (1H, d, J=16.2 Hz), 7.57 (1H, d, J=8.1 Hz), 7.25 (2H, d, J=8.0 Hz), 6.99 (1H, d, J=16.3 Hz), 6.47 (1H, d, J=2.0 Hz), 6.22 (1H, J=2.0 Hz), 5.06 (2H, s), 2.34 (3H, s). $^{13}$C-NMR (100 DMSO-d$_6$): δ 194.9, 178.0, 164.7, 161.6, 160.7, 156.8, 155.7, 143.2, 141.3, 136.8, 132.0, 131.9, 131.0, 129.1, 121.8, 121.0, 116.0, 104.5, 99.1, 94.2, 75.7, 21.5. ESI-MS m/z: 443.4 [M-H]$^-$

3.7 The synthesis of 3-O-[(E)-4-(3-Hydroxy-4-methoxyphenyl)-2-oxobut-3-en-1-yl]kaempferol (I-7)

After the above mentioned procedure (Example 3), the yellow solid was afforded from compound III-7 as starting material. Yield: 12.4%, $^1$H-NMR (400 MHz, DMSO-d$_6$): δ 12.57 (1H, s, OH), 10.89 (1H, s, OH), 10.27 (1H, s, OH), 9.25 (1H, s, OH), 8.05 (2H, d, J=8.4 Hz), 7.55 (1H, d, J=16.0 Hz), 7.12 (2H, s), 6.97 (1H, d, J=8.5 Hz), 6.92 (2H, d, J=8.4 Hz), 6.82 (1H, d, J 16.0 Hz), 6.47 (1H, s), 6.22 (1H, s), 5.02 (2H, s), 3.82 (3H, s). $^{13}$C-NMR (100 MHz, DMSO-d$_6$): δ 194.1, 177.5, 164.2, 161.1, 160.2, 156.3, 155.2, 150.4, 146.7, 143.1, 136.3, 130.5, 127.0, 121.8, 120.5, 119.7, 115.5, 114.2, 112.0, 104.0, 98.6, 93.7, 75.1, 55.6. ESI-MS m/z: 475.4 [M-H]$^-$

3.8 The synthesis of 3-O-[(E)-4-(3-Methoxy-4-hydroxyphenyl-)-2-oxobut-3-en-1-yl]kaempferol (I-8)

After the above mentioned procedure (Example 3), the yellow solid was afforded from compound III-8 as starting material. Yield: 13.5%. $^1$H-NMR (400 MHz, DMSO-d$_6$): δ 12.58 (1H, s, OH), 10.89 (1H, s, OH), 10.26 (1H, s, OH), 9.70 (1H, br s, OH), 8.06 (2H, d, J=8.8 Hz), 7.59 (1H, d, J=16.1 Hz), 7.30 (1H, d, J=1.5 Hz), 7.13 (1H, d, J=8.2 Hz, 1.5 Hz), 6.92 (2H, d, J=8.8 Hz), 6.90 (1H, d, J=16.1 Hz), 6.47 (1H, d, J=1.9 Hz), 6.22 (1H, d, J=2.0 Hz), 5.04 (2H, s), 3.82 (3H, s). $^{13}$C-NMR (100 MHz, DMSO-d$_6$): δ 194.5, 178.0, 164.7, 161.6, 160.7, 156.8, 155.7, 150.2, 148.4, 144.0, 136.8, 131.0, 126.2, 124.0, 121.0, 119.7, 116.1, 116.0, 112.0, 104.5, 99.1, 94.2, 75.5, 56.1. ESI-MS m/z: 475.4 [M-H]$^-$.

3.9 The synthesis of 3-O-[(E)-4-(4-(tert-Butyl)phenyl)-2-oxobut-3-en-1-yl] kaempferol (I-9)

After the above mentioned procedure (Example 3), the yellow solid was afforded from compound III-9 as starting material. Yield: 17.3%. $^1$H-NMR (400 MHz, DMSO-d$_6$): δ 12.55 (1H, s, OH), 10.84 (1H, s, OH), 10.25 (1H, s, OH), 8.06 (2H, s, J=2.0 Hz), 7.65 (1H, d, J=16.3 Hz), 7.60 (2H, d, 8.4 Hz), 7.46 (2H, d, J=8.4 Hz), 7.00 (1H, d, J=16.2 Hz), 6.93 (2H, d, J=9.0 Hz), 6.47 (1H, d, J=2.2 Hz), 6.22 (1H, d, J=2.0 Hz), 5.07 (2H, s), 1.29 (9H, s). $^{13}$C-NMR (100 MHz, DMSO-d$_6$) δ194.9, 178.0, 164.7, 161.6, 160.7, 156.8, 155.7, 154.2, 143.1, 136.8, 132.0, 131.0, 128.9, 126.3, 122.0, 121.0, 116.0, 104.5, 99.1, 94.2, 75.7, 35.1, 31.3. ESI-MS m/z: 485.2 [M-H]$^-$.

3.10 The synthesis of 3-O-[(E)-4-(4-Isopropylphenyl)-2-oxobut-3-en-1-yl] kaempferol (I-10)

After the above mentioned procedure (Example 3), the yellow solid was afforded from compound III-10 as starting material. Yield: 21.2%. $^1$H-NMR (400 MHz, DMSO-d$_6$): δ 12.55 (1H, s, OH), 8.05 (1H, d, 8.9 Hz), 7.64 (1H, d, J=16.2 Hz), 7.59 (2H, d, J=8.2 Hz), 7.30 (2H, d, J=8.2 Hz), 7.00 (1H, d, J=16.3 Hz), 6.93 (2H, d, J=8.9 Hz), 6.47 (1H, d, J=2.0 Hz), 6.22 (1H, d, J=2.0 Hz), 5.06 (2H, s), 2.91 (1H, m), 1.20 (6H, d, =6.9 Hz). $^{13}$C-NMR (100 MHz, DMSO-d$_6$): δ 194.9, 178.0, 164.7, 161.6, 160.7, 156.8, 155.7, 152.0, 143.2, 136.7, 132.3, 132.0, 131.0, 129.2, 127.4, 126.6, 116.0, 104.5, 99.1, 94.2, 75.7, 60.2, 33.9, 24.0, ESI-MS 471.2 [M-H]$^-$.

3.11 The synthesis of 3-O-[(E)-4-(3-Chloro-4-hydroxyphenyl)-2-oxobut-3-en-1-yl] kaempferol (I-11)

After the above mentioned procedure (Example 3), the yellow solid was afforded from compound as starting material. Yield: 13.5%. $^1$H-NMR (400 MHz, DMSO-d$_6$): δ 12.57 (1H, s, OH), 10.89 (2H, s, OH), 10.28 (1H, s, OH), 8.06 (2H, d, J=8.6 Hz), 7.75 (1H, s), 7.58 (1H, d, J=16.2 Hz), 7.50 (1H, d, J=8.5 Hz), 7.02 (1H, d, J=8.5 Hz), 6.93 (2H, d, J=8.7 Hz), 6.92 (1H, d, J=15.6 Hz), 6.48 (1H, s), 6.22 (1H, s), 5.04 (2H, s). $^{13}$C-NMR (100 MHz, DMSO-d$_6$): δ 194.1, 177.5, 164.2, 161.1, 160.2, 156.3, 155.5, 155.2, 141.6, 136.2, 130.5, 130.3, 128.8, 126.5, 120.5, 120.4, 120.3, 116.9, 115.5, 104.0, 98.6, 93.7, 75.1. ESI-MS m/z: 479.9 [M-H]$^-$.

3.12 The synthesis of 3-O-[(E)-4-(4-Cyanophenyl)-2-oxobut-3-en-1-yl] kaempferol (I-12)

After the above mentioned procedure (Example 3), the yellow solid was afforded from compound III-12 as starting material. Yield: 20.1%. $^1$H-NMR (400 MHz, DMSO-d$_6$): δ 12.53 (1H, s, OH), 10.89 (1H, s, OH), 10.25 (1H, s, OH), 8.04 (2H, d, J=8.9 Hz), 7.91-7.86 (4H, m), 7.70 (1H, d, J=16.4 Hz), 7.19 (1H, d, J=16.4 Hz), 6.47 (1H, d, J=2.0 Hz), 6.22 (1H, d, J=2.0 Hz), 5.10 (2H, s). $^{13}$C-NMR (100 MHz, DMSO-d$_6$) δ195.0, 177.9, 167.6, 164.7, 163.5, 161.6, 160.7, 159.0, 156.8, 155.7, 142.4, 140.8, 139.3, 136.7, 133.2, 133.1, 131.0, 129.6, 126.0, 121.0, 119.0, 116.0, 112.9, 104.5, 99.2, 94.2, 75.9. ESI-MS m/z: 453.9 [M-H]$^-$.

3.13 The synthesis of 3-O-[(E)-4-(4-Bromophenyl)-2-oxobut-3-en-1-yl] kaempferol (I-13)

After the above mentioned procedure (Example 3), the yellow solid was afforded from compound III-13 as starting material. Yield: 13.1%. $^1$H-NMR (400 MHz, DMSO-4): δ

12.53 (1H, s, OH), 10.87 (1H, s, OH), 10.25 (1H, s, OH), 8.04 (2H, d, J 8.7 Hz), 7.63 (4H, m), 7.07 (1H, d, J=16.3 Hz), 6.92 (2H, d, J=8.7 Hz), 6.47 (1H, d, J=1.5 Hz), 6.22 (1H, d, J=1.6 Hz), 5.07 (2H, s). $^{13}$C-NMR (100 MHz, DMSO-d$_6$): δ 194.9, 177.9, 164.7, 161.6, 160.7, 156.8, 155.7, 141.7, 136.7, 134.0, 132.4, 131.0, 130.9, 124.5, 123.6, 121.0, 116.0, 104.5, 99.2, 94.2. ESI-MS m/z: 507.6 [M-H]$^-$.

3.14 The synthesis of 3-O-[(E)-4-(4-Fluorophenyl)-2-oxobut-3-en-1-yl] kaempferol (I-14)

After the above mentioned procedure (Example 3), the yellow solid was afforded from compound III-14 as starting material. Yield: 19.2%. $^1$H-NMR (400 MHz, DMSO-d$_6$): δ 12.54 (1H, s, OH), 10.36 (1H, br s, OH), 10.00 (1H, br s, OH), 8.03 (2H, d, J=8.2 Hz), 7.75-7.65 (3H, m), 7.29-7.25 (2H, m), 7.00 (1H, d, J=16.0 Hz), 6.93 (2H, d, J=8.4 Hz), 6.50 (1H, s), 6.24 (1H, s), 5.06 (2H, s). $^{13}$C-NMR (100 MHz, DMSO-d$_6$) δ194.9, 177.9, 165.1, 164.9, 162.7, 161.6, 160.8, 156.8, 155.7, 141.9, 136.7, 131.4, 131.3, 131.0, 130.4, 122.8, 121.0, 116.6, 116.4, 116.0, 104.5, 99.2, 94.3, 75.7, 63.3. ESI-MS m/z: 447.1 [M-H]$^-$.

3.15 3-O-[(E)-4-(4-Chlorophenyl)-2-oxobut-3-en-1-yl] kaempferol (I-15)

After the above mentioned procedure (Example 3), the yellow solid was afforded from compound III-15 as starting material. Yield: 12.4%, $^1$H-NMR (400 MHz, DMSO-d$_6$): δ 12.60 (1H, s, OH), 10.97 (1H, br 5, OH), 10.34 (1H, br s, OH), 8.10 (2H, d, J=8.9 Hz), 7.76 (2H, d, J=8.5 Hz), 7.71 (1H, d, J=16.4 Hz), 7.55 (2H, d, J=8.5 Hz), 7.12 (1H, d, J=16.4 Hz), 6.97 (2H, d, J=8.9 Hz), 6.53 (1H, d, J=2.0 Hz), 6.27 (1H, d, J=2.0 Hz), 5.13 (2H, s). $^{13}$C-NMR (100 MHz, DMSO-d$_6$): δ 194.9, 178.0, 164.7, 161.6, 160.7, 156.8, 155.7, 141.7, 136.7, 135.7, 133.7, 131.0, 130.7, 129.5, 123.5, 121.0, 116.0, 104.5, 99.2, 94.2, 75.8, 63.3. ESI-MS m/z: 463.8 [M-H]$^-$,

3.16 The synthesis of 3-O-[(E)-4-(3,4-Dichlorophenyl)-2-oxobut-3-en-1-yl] kaempferol (I-16)

After the above mentioned procedure (Example 3), the yellow solid was afforded from compound III-16 as starting material. Yield: 24.5%. $^1$H-NMR (400 MHz, DMSO-d$_6$): δ 12.54 (1H, s, OH), 10.90 (1H, s, OH), 10.26 (1H, s, OH), 8.05 (2H, d, J=8.6 Hz), 8.02 (1H, s), 7.69 (2H, s), 7.63 (1H, d, J=16.3 Hz), 7.15 (1H, d, =16.3 Hz), 6.91 (2H, d, J=8.6 Hz), 6.47 (1H, s), 6.22 (1H, s), 5.08 (2H, s). $^{13}$C-NMR (100 MHz, DMSO-d$_6$): δ 194.4, 177.4, 170.3, 164.2, 161.1, 160.2, 156.3, 155.2, 139.7, 136.2, 135.1, 132.8, 131.8, 131.0, 130.5, 130.2, 128.3, 124.3, 120.5, 115.5, 112.8, 104.0, 98.6, 93.7, 75.3, 59.7. ESI-MS m/z: 498.3 [M-H]$^-$.

Formula 6

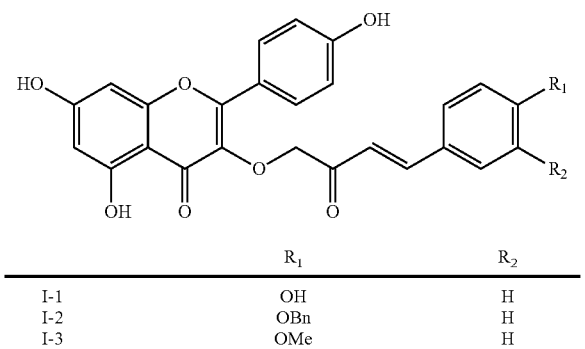

| | R$_1$ | R$_2$ |
|---|---|---|
| I-1 | OH | H |
| I-2 | OBn | H |
| I-3 | OMe | H |

Formula 6

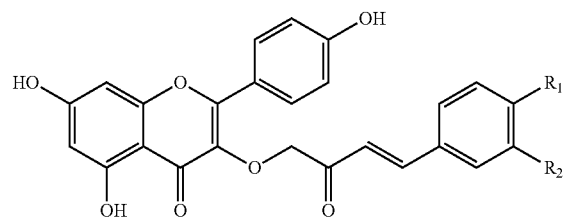

| | R$_1$ | R$_2$ |
|---|---|---|
| I-4 | OCH$_2$CH$_3$ | H |
| I-5 | H | H |
| I-6 | CH$_3$ | H |
| I-7 | OMe | OH |
| I-8 | OH | OMe |
| I-9 | t-Bu | H |
| I-10 | i-Pr | H |
| I-11 | OH | Cl |
| I-12 | CN | H |
| I-13 | Br | H |
| I-14 | F | H |
| I-15 | Cl | H |
| I-16 | Cl | Cl |

Example 4

Pharmacological Experiments 4.1 Glucose consumption assays in IR HepG2 cells 4.1.1 Method Pre-Treatment The compounds were dissolved in DMSO as stock. The final solution was 1:1,000 dilution of the stock in DMEM.

Human HepG2 cells were cultured in 96-well cluster plates, after achieving confluence, 10$^{-7}$ NI insulin was treated for 36 h in serum-free and phenol red-free high-glucose DMEM. After this incubation, the cells were washed four times with high-glucose DMEM (pH=4) and twice with phosphate-buffered saline. The cells were added to serum-free and phenol red-free high-glucose DMEM containing the various test compounds at different concentrations, incubated for 24 h, and then glucose content in the culture medium was measured using a glucose assay kit.

412 Test Index

The enhancement ratio of glucose consumption (GC) was calculated as follows: GC %=(GC treatment group−GC of control group)/GC of control group×100.

The potencies of the products were expressed as median effective concentration (EC50) values.

Statistical Analysis

All data were presented as the means±SD. SPSS10.0 was used for statistical analysis. Statistical significance was at a level of 5% (p<0.05).

4.1.3 Results

The tested compounds showed significant effects on enhancing glucose consumption in IR HepG2 cells (Table 4.1). Compound I-12 revealed the strongest antidiabetic activity, and had greater than that of marketed drug metformin.

TABLE 4.1

Effects on glucose consumption of compounds I in IR HepG2 cells

| Compound | EC$_{50}$(μM) | Compound | EC$_{50}$(μM) |
|---|---|---|---|
| I-1 | 0.368 | I-9 | 0.013 |
| I-2 | 0.658 | I-10 | 0.015 |
| I-3 | 0.149 | I-11 | 3.555 |
| I-4 | 0.042 | I-12 | 0.003 |
| I-5 | 0.473 | I-13 | 0.393 |
| I-6 | 0.010 | I-14 | 0.669 |
| I-7 | 5.070 | I-15 | 1.075 |
| I-8 | 6.190 | I-16 | 2.587 |
| metformin | 0.270 | | |

4.2. Screening of Anti-Diabetic Compounds in GLUT4myc Expressing Skeletal Muscle Cell Line L6-GLUT4myc: The Stimulation of GLUT4 Translocation by Flavonoid Derivatives 4.2.1 Principle GLUT4 is the main glucose transporter in skeletal muscle. In the basal state, the majority of GLUT4 locate in vesicles of cytoplasma. In response to insulin, GLUT4 translocates to the cell membrane, therefore transport more glucose into cell. The rate of glucose transport is the rate-limiting step of glucose metabolism in skeletal muscle. Hence, the amount of GLUT4 on the cell membrane reflects the amount of glucose uptake by the cell. In order to measure GLUT4 translocation, we use stable over expressing GLUT4myc rat muscle cell line, L6-GLUT4myc. The amount of GLUT4 on intact cell membrane was measured by ELISA with anti-myc antibody and HRP-conjugated secondary antibody. The OD value was detected at 492 nm.

4.2.2 Method

Pre-Treatment

The tested compounds were dissolved in DMSO as stock. The final solution was 1:1,000 dilution of the stock in low glucose DMEM.

The cells were treated with each compound at 2 to 5 different concentrations with triplicate in each group. The control group was treated with 0.1% DMSO. The blank group had no treatment. Insulin was used as positive control.

4.2.3 Measurement of Cell Surface GLUT4myc Density

Myoblasts were cultured and differentiated into myotubes. Cells were serum starved for 4 hours, then incubated with different compounds at different concentrations for 24 hours or with 100 nM insulin for 20 min. Then cells were washed 3 times with ice-cold phosphate-butfered saline (PBS) supplemented with 1 mM Ca2+ and 1 mM Mg2+(PBS+), fixed with 3% (v/v) paraformaldehyde (PFA) in PBS+ for 10 min at 4° C., then 20 min at room temperature. The cells were washed twice with PBS+, quenched 10 min with 100 mM glycine in PBS+, blocked 10 min with ice-cold 5% (v/v) milk in PBS+, and reacted with polyclonal anti-myc antibody (1:250) for 1 hour. After washing 6 times with PBS+, cells reacted with HRP-bound goat anti-rabbit secondary antibody (1:5000) for 1 hour. The cells were washed 6 times with PBS+, and incubated with 1.0 ml OPD reagent and allowed to develop for 10-20 min. The reaction was stopped with 0.25 ml per well of 3 M HCl. Supernatants were collected and absorbance was measured at 492 nm. Background absorbance obtained in the absence of anti-myc antibody was subtracted from all values.

Statistical Analysis

All data were presented as the means±SD. SPSS16.0 was used for statistical analysis. Data sets of more than two groups were compared using analysis of variance (One-Way ANOVA). Statistical significance was at a level of 5% (p<0.05).

4.2.4 Results

Figure 2:
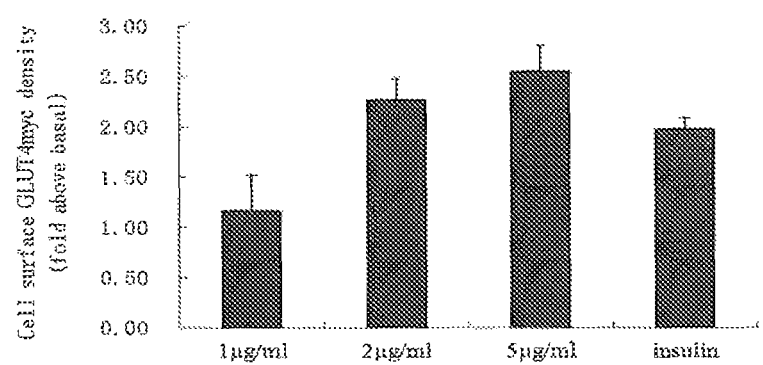
FIG. 2. Promoting effect of compound I-12 with different concentrations on GLUT4myc translocation in the skeletal muscle cells.

As shown in FIG. 1 and FIG. 2, the flavonoid derivatives significantly stimulate GLUT4myc translocation in L6-GLUT4myc muscle cells which means they can promote glucose metabolism in muscle. Among these compounds, compound I-12 has the strongest effect. At 2 μg/ml and 5 μg/ml, it has higher effect on GLUT4 translocation than insulin.

4.3 Effects of Flavonoid Derivative on Phosphorylation of AMPK and ACC by Western Blotting 4.3.1 AMPK Signal Pathway in Diabetes AMP-activated protein kinase (AMPK) has been proposed as a 'fuel gauge', capable of sensing the energy status in both individual cells and the whole body. Once AMPK is activated by the increase of the AMP:ATP ratio, AMPK promotes the switch from anabolic to catabolic metabolism. The activation of AMPK can increase skeletal muscle glucose uptake, fatty acid oxidation in muscle and mitochondria biogenesis, play in regulating glucose and lipid metabolism. It has been approved that the activation of AMPK by exercise, hypoxia, or the increase of osmotic pressure could promote glucose uptake by stimulating GLUT4 translocation to the plasma membrane.

Acetyl CoA carboxylase (ACC) is one of the direct protein substrates of AMPK. It can catalyze the irreversible carboxylation of acetyl-CoA to produce malonyl-CoA, which can indirectly inhibit fatty acid oxidation in the mitochondria to regulate lipid metabolism. In addition, AMPK inhibits ACC through phosphorylation to inhibit adipogenesis.

In this section, Western Blotting was used to assay the effect of these flavonoids on the phosphorylation of AMPK and ACC in HepG2 cells to illustrate the relationship between the mechanism of the flavonoids on glucose uptake and lipid metabolism and APMK signal pathway.

4.3.2 Experimental Procedure

Whole cell lysate preparation: After serum-starving HepG2 cells, the cells were incubated with the flavonoids for 2 h, and then washed twice with PBS. Next, pre-chilled RIPA lysis buffer was added for 20 min at 4° C. The lysates were centrifuged at 13,000 rpm/min for 10 min at 4° C., and the supernatants were used for determination of total protein content. Forty micrograms of protein from the supernatant was aliquoted and its volume was adjusted to thirty microliters using deionized water and loading buffer. Lastly, the protein samples were heated at 65° C. for 15 min.

Western blot analysis: The samples were electrophoresed on 7.5% SDS-polyacrylamide gels, transferred to polyvinylidene fluoride membranes, blocked for 1 h in 5% (w/v) bovine serum albumin, and then incubated with primary antibodies overnight at 4° C. The membranes were washed three times with TBST and incubated with appropriate secondary antibodies conjugated to horse-radish peroxidase for 1 h at room temperature. The immunoreactive bands were detected using chemiluminescent reagent and autoradiographic film.

4.3.3 Results

Figure 3:
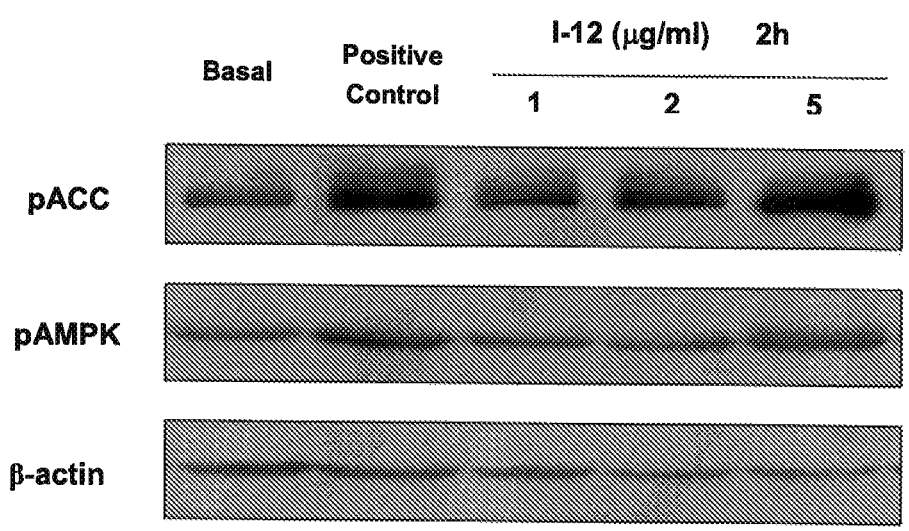
FIG. 3. Effects of compound I-12 on phosphorylation of AMPK and ACC by western blotting.
Figure 4:
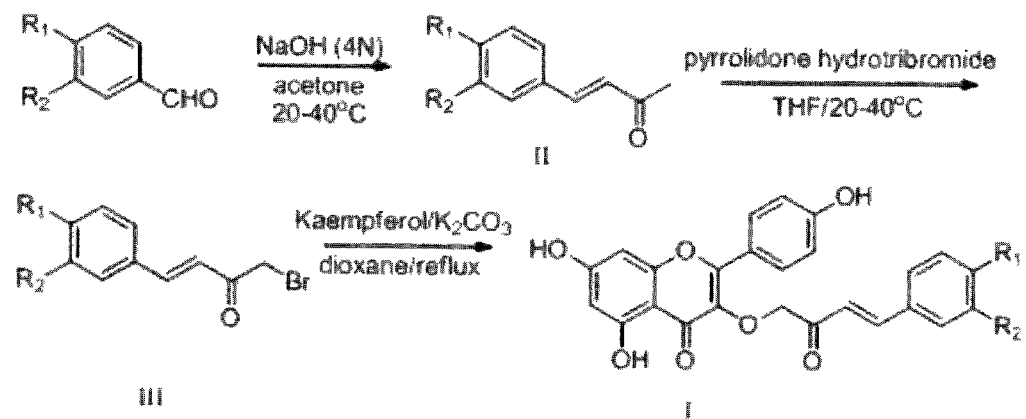
FIG. 4. Preparative method of the flavonoid compounds or a pharmaceutically acceptable salt thereof.

According to the FIG. 3, the compound I-12 can significantly stimulate the phosphorylation of AMPK and ACC which is the downstream of AMPK in the Hep-G2 cells, The above results of pharmacological experiments show that the flavonoid derivatives synthesized in the present invention can enhance the glucose consumption and increase glucose uptake in the insulin resistance Hep-G2 cells. Moreover, the derivates I-2, I-3, I-10, I-12, and I-14 significantly stimulate GLUT4myc translocation in L6-GLUT4myc muscle cells, promoting glucose uptake in muscle cells. It indicated that the flavonoid derivatives of the present invention have anti-diabetic effects and can be used for treatment of diabetes.

In particular, in the claimed anti-diabetic compounds of the present invention, the inventors surprisingly found that the preferred compounds, for example, when R2 group is H, the compounds I-1, I-3, I-4, I-6, I-9, I-10, I-11, I-12 and I-13 exhibits comparable activity with that of metformin. In addition, compounds I-3, I-4, I-6, I-9, I-10, and I-12 are significantly superior to that of metformin.

Further evaluation on glucose transporter 4 translocation in skeletal muscle cells (L6 GLUT4myc) and AMPK pathway associated proteins phosphorylation reveals that the active compounds of the present invention have anti-diabetic activity, especially compound I-12 have the strongest effect on promoting glucose transporter 4 translocation than insulin at the concentrations of 2, and 5 µg/mL in skeletal muscle cells. On the other hand, the claimed flavonoid derivatives significantly promoted glucose transporter 4 translocation in skeletal muscle cells, strongly activates AMPK in that it increases the phosphorylation of both AMPK and ACC in IR HepG2 cells, that is one of the mechanisms of the anti-diabetic effect, and has firstly demonstrated in the present invention.

Many researchers have been looking for compounds with anti-diabetic activities, a type of the compound with an acceptable activity for drug discovery has important significance for the preparation of anti-diabetic drugs. From the claimed compounds in the present invention, the substituents of flavone skeleton are all defined as hydroxyl groups, and bonded via methylene substituted cinnamoyl group at the position of C-3, forming the structure of 3-O-[(E)-4-(4-substituted-phenyl)-2-oxobut-3-en-1-yl] kaempferol. This structure is very different from disclosed anti-diabetic compounds by now. It is difficult for the researcher whom obtains the claimed compounds of the present invention according to above mentioned approach on the basis of general structure of flavonoid. Accordingly, the claimed compounds of the present invention is not be obviously inferred by related researchers.

Furthermore, since the substituted groups of flavonoid derivatives are limited to very strict in the present invention, in which the number of the compounds is very limited, and wherein the preferred compounds evaluating by several pharmacological methods revealed the acceptable anti-diabetic activity for drug discovery. Thus, the present invention has had a remarkable progress.

In particular, preferred compounds of the present invention exhibits comparable activity or stronger with that of metformin. Specifically, at 2 µg/ml and 5 µg/ml, compound I-12 has higher effect on GLUT4 translocation than insulin in skeletal muscle cells. Furthermore, the molecular mechanism of anti-diabetic effect of flavonoid derivatives is first discovered. According to the current technologies, the above results are impossible to predict and infer by related researchers. On the consideration of the general anti-diabetic compounds, the present invention has more important application value.

What is claimed is:

1. A compound of formula 1, or a pharmaceutically acceptable salt thereof:

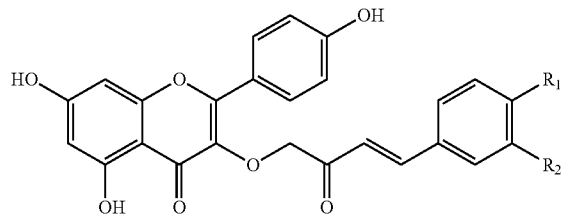

Formula 1

R1 and R2 are the same or different, each independently, hydrogen, halogen, cyano, hydroxy, benzyloxy, $C_{1-8}$alkyl, $C_{1-8}$alkyl with halogen substituted or $C_{1-8}$alkoxy wherein $C_{1-8}$alkyl is an alkyl having 1-8 carbons—that is, 1, 2, 3, 4, 5, 6, 7 or 8 carbons in a linear or branched chain, $C_{1-8}$alkyl with halogen substituted is an alkyl with halogen substituted having 1-8 carbons—that is, 1, 2, 3, 4, 5, 6, 7 or 8 carbons in a linear or branched chain and $C_{1-8}$alkoxy is an alkoxy having 1-8 carbons—that is, 1, 2, 3, 4, 5, 6, 7 or 8 carbons in a linear or branched chain.

2. A compound according to claim 1, or a pharmaceutically acceptable salt thereof, wherein R2 is hydrogen, hydroxyl or $C_{1-8}$alkoxy in a linear or branched chain.

3. A compound according to claim 1, or a pharmaceutically acceptable salt thereof, wherein R2 is hydrogen.

4. The compounds according to claim 1, or a pharmaceutically acceptable salt thereof, wherein the structure is shown as follows:

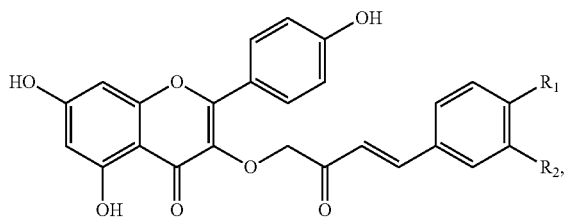

wherein a combination of $R_1$ and $R_2$ is selected from the group consisting of $R_1$ is OH and $R_2$ is H (I-1), $R_1$ is OBn and $R_2$ is H (I-2), $R_1$ is OMe and $R_2$ is H (I-3), $R_1$ is OCH$_2$CH$_3$ and $R_2$ is H (I-4), $R_1$ is H and $R_2$ is H (I-5), $R_1$ is CH$_3$ and $R_2$ is H (I-6), $R_1$ is OMe and $R_2$ is OH (I-7), $R_1$ is OH and R2 is OMe (I-8), $R_1$ is t-Bu and $R_2$ is H (I-9), $R_1$ is i-Pr and $R_2$ is H (I-10), $R_1$ is OH and $R_2$ is Cl (I-11), $R_1$ is CN and $R_2$ is H (I-12), $R_1$ is Br and $R_2$ is H (I-13), $R_1$ is F and $R_2$ is H (I-14), $R_1$ is Cl and $R_2$ is H (I-15), and $R_1$ is Cl and $R_2$ is Cl (I-16).

5. A compound according to claim 4, or a pharmaceutically acceptable salt thereof, wherein $R_1$ and $R_2$ are defined by a combination selected from the group consisting of I-3, I-4, I-6, I-9, I-10, and I-12.

6. A compound according to claim 4, or a pharmaceutically acceptable salt thereof, wherein $R_1$ and $R_2$ are defined by I-12.

7. A composition for treating diabetes in a patient in need thereof, comprising a therapeutically effective amount of a compound according to claim 1, or a pharmaceutically acceptable salt thereof, and a pharmaceutically acceptable carrier.

8. A method for preparation of the compounds of claim 1 comprising:

(a) mixing an NaOH aqueous solution with a solution of substituted benzaldehydes in acetone, followed by removal of excess acetone;
(b) adjusting the pH of the resulting solution to a neutral value;
(c) extracting the resulting mixture and then drying the resulting solution, followed by filtration and removal of a solvent of the filtrate;
(d) purifying a resulting crude product to give the compound of formula II,

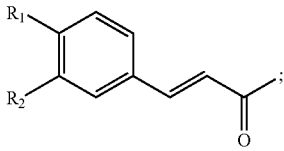

(e) mixing a solution of pyrrolidonehydrotribromide in THF with a solution of the compound of formula II in THF, followed by removal of a solvent and purification of a resulting crude product to give the compound of formula III

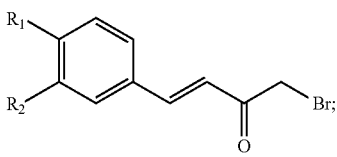

(f) mixing a solution of the formula III in 1,4-dioxane with a mixture of kaempferol and $K_2CO_3$ in 1,4-dioxane, followed by removal of a solvent;

(g) adding water, acidifying a resulting aqueous phase and then performing extraction with ethyl acetate;
(h) drying, filtering and concentrating an organic phase of the mixture; and
(i) purifying a resulting crude product.

9. The method of claim 8, wherein in step (a), the NaOH aqueous solution is a 4N NaOH aqueous solution.

10. The method of claim 8, wherein in step (a), after mixing the NaOH aqueous solution with the solution of substituted benzaldehydes in acetone, the mixture is stirred at 25 to 40° C. in 15 minutes to 12 hours.

11. The method of claim 8, wherein in step (c), the resulting mixture is extracted with ethyl acetate and the resulting solution is dried over anhydrous $MgSO_4$.

12. The method of claim 8, wherein in step (d), the purifying of the resulting crude product is performed by recrystallization or column chromatography.

13. The method of claim 8, wherein in step (e), the purification of the resulting crude product is performed by chromatography on silica gel.

14. The method of claim 11, wherein in step (f), the mixture of kaempferol and $K_2CO_3$ in 1,4-dioxane is stirred for 1 hour while maintaining a reflux before adding the solution of the formula III in 1,4-dioxane.

15. The method of claim 8, wherein in step (f), the solution of the formula III in 1,4-dioxane with the mixture of kaempferol and $K_2CO_3$ in 1,4-dioxane are mixed for 1.5 to 12 hours.

16. The method of claim 8, wherein in step (f), the solvent is removed from the reaction mixture under reduced pressure.

17. The method of claim 8, wherein in step (i), the resulting crude product is purified using a gel-permeation chromatography and preparation-thin layer chromatography.

* * * * *